US007515961B2

(12) United States Patent
Germanson et al.

(10) Patent No.: US 7,515,961 B2
(45) Date of Patent: Apr. 7, 2009

(54) METHOD AND APPARATUS FOR DYNAMICALLY MONITORING, DETECTING AND DIAGNOSING LEAD CONDITIONS

(75) Inventors: Nancy M. Germanson, Maple Grove, MN (US); Thomas H. Spear, Bloomington, MN (US); Alan R. Braly, Minneapolis, MN (US); Rick D. McVenes, Isanti, MN (US)

(73) Assignee: Medtronic, Inc., Minneapolis, MN (US)

( * ) Notice: Subject to any disclaimer, the term of this patent is extended or adjusted under 35 U.S.C. 154(b) by 301 days.

(21) Appl. No.: 11/119,529

(22) Filed: Apr. 29, 2005

(65) Prior Publication Data

US 2006/0247706 A1 Nov. 2, 2006

(51) Int. Cl.
*A61N 1/08* (2006.01)

(52) U.S. Cl. .......................... 607/27; 607/28; 600/547

(58) Field of Classification Search ............. 607/27–28; 600/547
See application file for complete search history.

(56) References Cited

U.S. PATENT DOCUMENTS

| | | | | |
|---|---|---|---|---|
| 4,825,869 A | | 5/1989 | Sasmor et al. ......... 128/419 PT |
| 4,899,750 A | | 2/1990 | Ekwall ................. 128/419 PG |
| 5,052,388 A | | 10/1991 | Sivula et al. .......... 128/419 PG |
| 5,345,362 A | | 9/1994 | Winkler ....................... 361/681 |
| 5,476,483 A | * | 12/1995 | Bornzin et al. ................. 607/17 |
| 5,660,183 A | | 8/1997 | Chiang et al. ........... 128/695 R |
| 5,814,088 A | * | 9/1998 | Paul et al. ...................... 607/28 |
| 5,891,179 A | | 4/1999 | Er et al. ......................... 607/27 |
| 5,944,746 A | * | 8/1999 | Kroll ............................. 607/27 |
| 6,129,746 A | | 10/2000 | Levine et al. .................. 607/27 |
| 6,317,633 B1 | | 11/2001 | Jorgenson et al. ............. 607/28 |
| 6,445,951 B1 | | 9/2002 | Mouchawar |
| 6,490,486 B1 | * | 12/2002 | Bradley ........................ 607/28 |
| 6,721,600 B2 | | 4/2004 | Jorgenson et al. ............. 607/27 |
| 2002/0120307 A1 | * | 8/2002 | Jorgenson et al. ............. 607/27 |
| 2004/0064161 A1 | | 4/2004 | Gunderson et al. ............ 607/28 |
| 2004/0172082 A1 | | 9/2004 | Ferek-Petric ................. 607/27 |

\* cited by examiner

*Primary Examiner*—Carl H. Layno
*Assistant Examiner*—Yun Haeng Lee
(74) *Attorney, Agent, or Firm*—Michael C. Soldner

(57) ABSTRACT

The present invention provides diverse methods and apparatus for in vivo monitoring, detecting and/or predicting potential failure modes or deleterious trends of chronically implanted medical electrical leads prior to actual failure of said leads. Certain embodiments of the invention involve applying a relatively increased data sampling rate at various time intervals (e.g., periodically, randomly, and/or manually-triggered and the like) prior to actual detection of a deleterious trend, to thereby increase the probability of detecting one or more parameters indicative of a potential lead performance issue. At least some of the parameters are utilized because they are not typically reliably detected at relatively lower data sampling rates. In addition to an initial relatively increased data sampling rate, certain embodiments provide for adjusting the sampling rate and storing and/or adjusting data pattern template-based data to execute pattern related triggers so that additional information regarding a medical electrical lead can be obtained.

20 Claims, 7 Drawing Sheets

METHOD AND APPARATUS FOR DYNAMICALLY MONITORING, DETECTING AND DIAGNOSING LEAD CONDITIONS

FIELD

The present invention relates to implantable medical devices, and, more particularly, implantable medical devices utilizing leads.

BACKGROUND

A wide variety of implanted medical devices (IMDs) for delivering a therapy or monitoring a physiologic condition which can employ one or more elongated electrical leads and/or sensors are available. Such IMDs can monitor or deliver therapy to the heart, muscle, nerve, brain, and stomach or other organs. IMDs such as pacemakers and implantable cardioverter defibrillators (IMDs), are available for treating cardiac arrhythmias by delivering electrical impulses to the heart. Such devices sense electrical cardiac activities through cardiac leads having electrode(s). When an abnormal rhythm is detected, an appropriate electrical therapy is delivered.

Leads associated with such IMDs typically include a lead body extending between a proximal lead end and a distal lead end and incorporates one or more exposed electrode or sensor elements located at or near the distal lead end. One or more elongated electrical conductors extend through the lead body from a connector assembly provided at a proximal lead end for connection with an associated IMD and an electrode located at the distal lead end or along a section of the lead body. Each electrical conductor is typically electrically isolated from any other electrical conductors and is encased within an outer sheath that electrically insulates the lead conductors from body tissue and fluids.

Implantable medical leads can extend from a subcutaneous implantation site of the IMD through an internal body pathway to a desired tissue site. The leads are generally preferred having small diameter, highly flexible, reliable lead bodies that withstand degradation by body fluids and body movements that apply stress and strain to the lead body and the connections made to electrodes. As lead bodies are made smaller and smaller and the number of lead conductors is increased or maintained, the integrity of lead conductors is increasingly important.

Cardiac lead bodies are continuously flexed by the beating of the heart. Other stresses are applied to the lead body during an implantation or lead repositioning procedure. Movements by the patient can cause the route traversed by the lead body to be constricted or otherwise altered causing stresses on the lead body. At times, the lead bodies can be slightly damaged during surgical implantation, and the slight damage can progress in the body environment until a lead conductor fractures and/or the insulation is breached. The effects of lead body damage can progress from an intermittent manifestation to a more continuous effect. In extreme cases, insulation of one or more of the electrical conductors can be breached, causing the conductors to contact one another or body fluids resulting in a low impedance or short circuit. In other cases, a lead conductor can fracture and exhibit an intermittent or continuous open circuit resulting in an intermittent or continuous high impedance.

Other issues can arise at the proximal lead end where the electrical connection between IMD connector elements and the lead connector elements can be intermittently or continuously disrupted, resulting in a high impedance or open circuit. Usually, such connector open circuit problems result from insufficient tightening of the connection mechanisms, such as a set screw, at the time of implantation followed by a gradual loosening of the connection until contact becomes intermittent or open or an incomplete lead pin insertion.

Such lead issues resulting in short or open circuits, for example, can be referred to, for simplicity, as "lead related conditions." Typically, it is necessary for an attending clinician to diagnose the nature of a lead related condition from available data, test routines, and patient symptoms. Then, it is necessary for the clinician to take corrective action, e.g., to either replace the lead, select different electrodes for sensing or pacing, or tighten the proximal connection. In severe cases, the lead related condition can result in premature depletion of the battery energy of the IMD, requiring its replacement.

In the case of cardiac leads, the ability to sense cardiac activity conditions accurately through a lead can be impaired by any of the above described lead related conditions. Complete lead breakage impedes any sensing functions while lead conductor fractures or intermittent contact can cause electrical noise that interferes with accurate sensing. Oversensing or undersensing can result in an incorrect interpretation of the cardiac data potentially resulting in inappropriate withholding or delivery of electrical therapy. During cardiac pacing or defibrillation, increased impedance of the stimulation path or the short circuit of lead conductors due to one of the above-described lead related conditions can reduce the effectiveness of a pacing or defibrillation below that sufficient to pace or defibrillate the heart.

Certain pacemakers and IMDs have been provided with the capability of storing cardiac electrogram data prompted by the automatic determination of oversensing or undersensing of cardiac events, loss of capture, out of range lead impedance measurements, etc. Such data is telemetered to an external instrument when the physician interrogates the IMD and used by the clinician in troubleshooting problems. The lead impedance data and other parameter data is typically compiled and displayed on a monitor and/or printed out for analysis by the clinician. The clinician can undertake real time IMD parameter reprogramming and testing and observe the monitored surface ECG, if the IMD is an ICD, to try to pinpoint a suspected lead related condition that is indicated by the data and/or patient and/or device symptoms. Certain external instruments that address the analysis of such data and symptoms include those disclosed in U.S. Pat. No. 4,825,869 (Sasmor et al.); U.S. Pat. No. 5,660,183 (Chiang et al.); and U.S. Pat. No. 5,891,179 (Er et al.), all of which are incorporated herein by reference.

SUMMARY

The present invention provides diverse methods and apparatus for in vivo monitoring, detecting and/or predicting potential failure modes or deleterious trends of chronically implanted medical electrical leads prior to actual failure of said leads. Certain embodiments of the invention involve applying a relatively increased data sampling rate at various time intervals (e.g., periodically, randomly, aperiodically, and/or manually-triggered and the like) prior to actual detection of a deleterious trend, to thereby increase the probability of detecting one or more parameters indicative of a potential lead performance issue. At least some of the parameters are utilized because they are not typically reliably detected at relatively lower data sampling rates.

In addition to an initial relatively increased data sampling rate, certain embodiments of the invention provide for adjusting the sampling rate and storing and/or adjusting data pattern template-based data to execute pattern related triggers so that additional information regarding a medical electrical lead can be obtained.

The invention provides several advantages particularly for medical electrical leads that have reliably operated for a relatively lengthy term (e.g., several years to more than about ten years). One aspect of the invention involves the fact that the trends and parameters utilized to interrogate a lead can be effectively customized for a given patient thereby potentially further decreasing the amount of time before a performance issue with a lead is declared. Another way of expressing the advantage relates to the fact that a possible performance issue can be detected sooner allowing for, as applicable, manual intervention or re-programming of the parameters (e.g., sensing, detection, thresholds, etc.) of a device coupled to the lead by a clinician. In this scenario the sampled and stored data (historical and current) about a lead is available to the clinician thereby likely improving the accuracy of the re-programming, if necessary.

In a related aspect, in lieu of manually re-programming by a clinician the implantable medical device (IMD) coupled to a suspect lead can automatically resolve the difficulty and/or set a warning flag, telemeter a patient alert signal, or the like. Along the lines of the foregoing, another aspect of the invention provides for an elective replacement indicator (ERI) feature. According to this aspect of the invention, wherein in the event that one or more monitored lead parameters exceeds a single-parameter threshold or two or more parameters exceed an aggregated multiple parameter threshold, for example, the device suitably stores and/or telemeters a message indicating replacement of one or more leads. The message can cover a continuum of performance metrics (e.g., replacement required, replacement suggested for next follow-up appointment, replacement at next device change-out, etc.).

Because medical electrical leads can effectively operate for a long time, it is not uncommon for several devices to sequentially utilize a single set of leads. Thus, the invention contemplates a wireless upgrade feature wherein a device programmer can not only upload the lead status and historically sampled data, but can also affirmatively reprogram or upgrade the then-present lead verification and monitoring software.

The invention can of course be utilized to assist following of human patients over extended periods of time, but can also be utilized in the context of following shorter term research subjects (e.g., human and animal). In the later example, a complex research lead can be non-invasively interrogated with high rate sampling to ensure accurate and consistent lead performance during a research protocol.

The foregoing summary information is intended to merely illustrate some of the advantages and features of the invention and is not meant to limit the scope of the invention in any way. In fact, upon review of the foregoing and the following described and depicted embodiments one of skill in the art will surely recognize insubstantial modifications or extensions of the invention each of which is expressly intended to be covered hereby.

DETAILED DESCRIPTION

Figure 1:
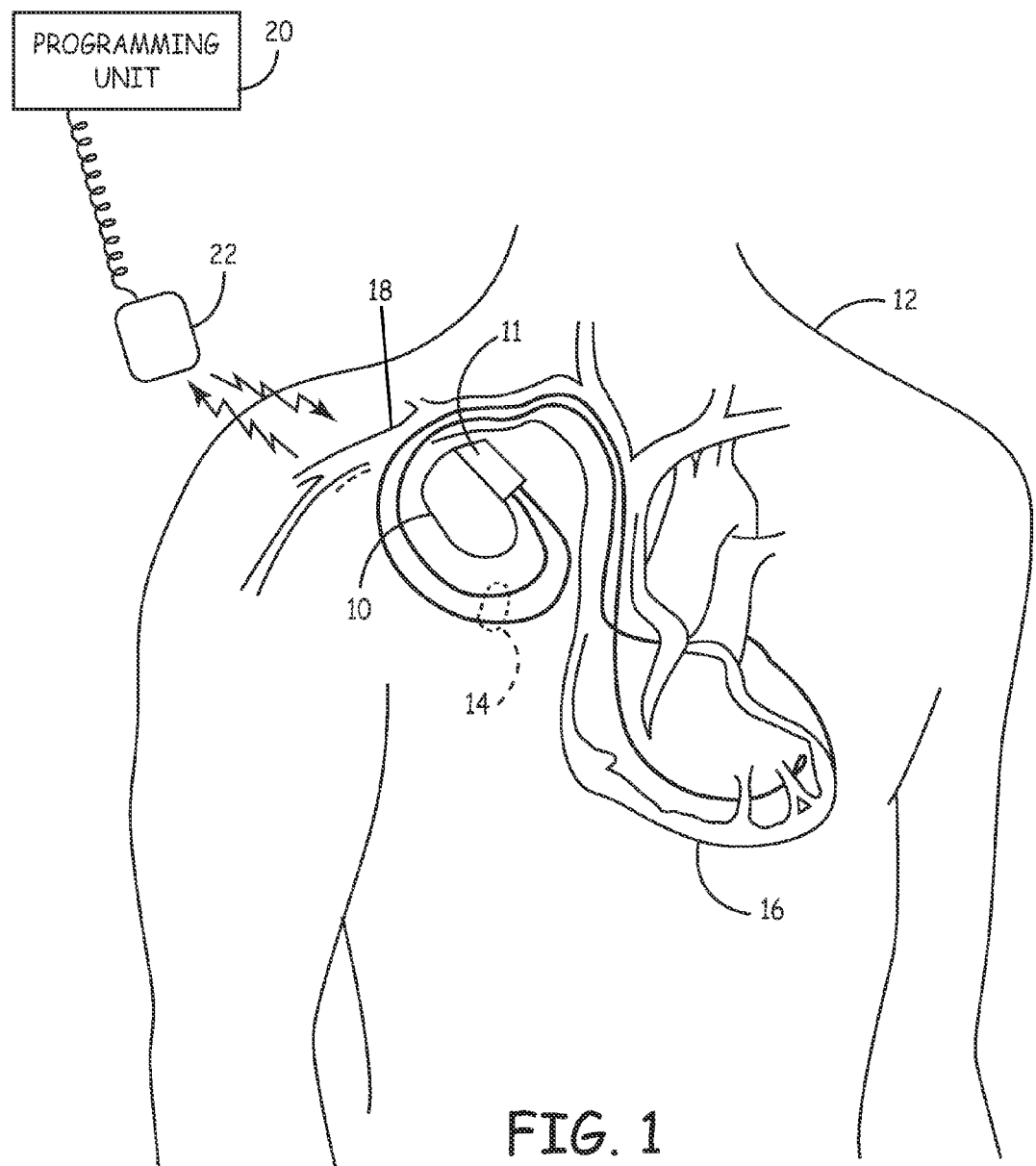
FIG. 1 is an illustration of an implantable medical device capable of pacemaking, cardioversion, and defibrillation in communication with a patient's heart via a stimulation and/or sensing leads in which the embodiments of the invention can be implemented.

The following discussion is presented to enable a person skilled in the art to make and use the embodiments of the invention. Various modifications to the illustrated embodiments will be readily apparent to those skilled in the art, and the generic principles herein can be applied to the embodiments and applications without departing from the spirit and scope of the embodiments of the invention as defined by the appended claims. Thus, the embodiments of the invention are not intended to be limited to those shown, but are to be accorded the widest scope consistent with the principles and features disclosed herein. The following detailed description is to be read with reference to the figures, in which like elements in different figures have like reference numerals. The figures, which are not necessarily to scale, depict embodiments and are not intended to limit the scope of the inventions. Skilled artisans will recognize the examples provided herein have many useful alternatives, which fall within the scope of the invention.

The embodiments of the invention are aimed at providing a system and method for automatically monitoring, detecting and suggesting a diagnosis of lead related conditions based on search and discover surveillance methods that can include initial high frequency data sampling and use of lead related patterns stored in templates for correlations. The systems and methods included in the embodiments of the invention can be used in conjunction with, or incorporated in, an implantable medical device (IMD), such as a pacemaker, defibrillator, and other devices using a lead for stimulating, sensing, and/or monitoring parameters. Preferably, methods included in the embodiments of the invention are fully implemented in an IMD itself. Alternatively, methods included in the embodiments of the invention can be implemented in an external device capable of receiving stored data through uplinking telemetry.

FIG. 1 is an illustration of a medical device system adapted for use in accordance with the embodiments described herein. The medical device system includes an implantable device 10 (e.g., a pacemaker or cardiovector/defibrillator, for example) that has been implanted in a patient 12. Device 10 is housed within a hermetically sealed, biologically inert outer casing, which by itself can be conductive so as to serve as an indifferent electrode in the device's pacing/sensing circuit. One or more leads, collectively identified with reference numeral 14 are electrically coupled to the device 10 in a conventional manner and extend into a patient's heart 16 via a vein 18. The leads can provide both sensing and stimulation. Disposed generally near the distal ends of leads 14 are one or more exposed conductive electrodes for receiving electric cardiac signals and/or for delivering electrical pacing stimuli to heart 16. Leads 14 can be implanted with their distal ends situated in the atrium and/or ventricle of heart 16 as well as on the outside surface of the heart 16 or within any vasculature on or around the heart 16. They can also be implanted subcutaneously.

Also depicted in FIG. 1 is an external programming unit 20 for non-invasive communication with IMD 10 via uplink and downlink communication channels as is well known to those of ordinary skill in the art. Associated with the programming unit 20 is programming head 22, in accordance with a conventional medical device programming system, for facilitating two-way communication between the IMD 10 and instrument 20. An example of instrument 20 is described in U.S. Pat. No. 5,345,362, which is hereby incorporated by reference.

The embodiments of the invention are not limited to the particular IMD shown in FIG. 1, however, but can be practiced by any number of implantable devices. The techniques of the invention can be practiced by a device that paces, senses, and/or monitors a single cardiac chamber or several chambers; that pace, sense, and/or monitor one or more atria or one or more ventricles; that includes or lacks cardioversion and defibrillation capability; and that paces in any pacing mode.

The electrodes on the leads can be used as a bipolar pair, commonly referred to as a "tip-to-ring" configuration, or individually in a unipolar configuration with the device housing 10 serving as the indifferent electrode, commonly referred to as the "can" or "case" electrode. The device housing 10 can also serve as a subcutaneous defibrillation electrode in combination with a defibrillation coil electrode (not shown) for defibrillation of the heart. It is recognized that alternate lead configurations can be substituted for the right ventricular lead illustrated in FIG. 1.

It is to be understood that methodologies included in the embodiments of the invention can be adapted for use with any single chamber device and can be expanded for use with dual chamber, or multichamber ICD or pacemaker systems including multiple leads each carrying one or more electrodes. The methodologies included in the embodiments of the invention can alternatively be used in other types of electrical pulse generator systems that require implantable leads for stimulating or sensing excitable body tissue, such as neurological applications, for example.

Figure 2:
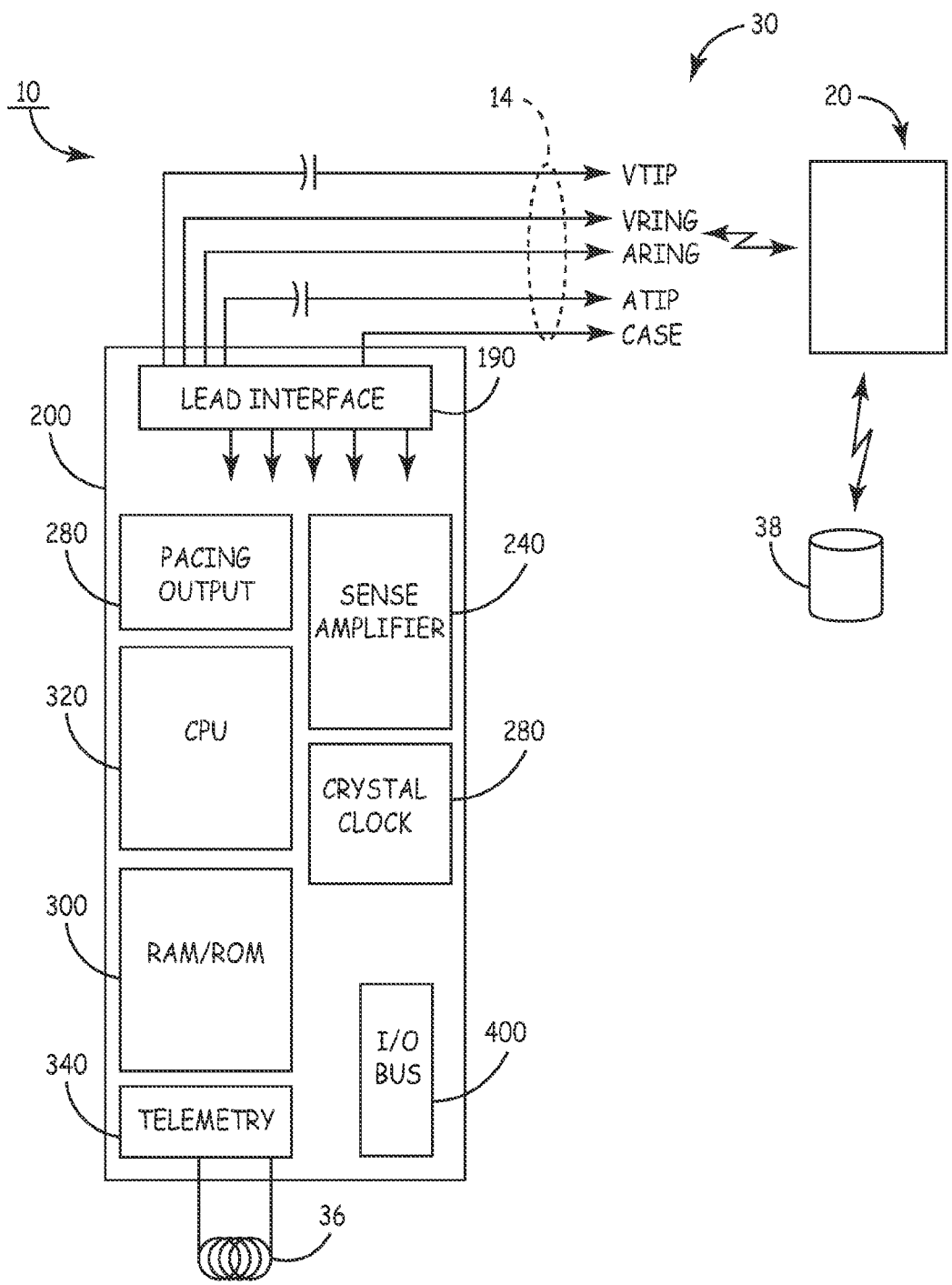
FIG. 2 is a functional, block diagram of the lead monitoring system, in which methods included in the embodiments of the present invention can be implemented.

A functional schematic diagram the IMD 10 of FIG. 1 is shown in FIG. 2. This diagram should be taken as exemplary of the type of device with which the invention can be embodied and not as limiting. The disclosed embodiment shown in FIG. 2 is a microprocessor-controlled device, but the methods of the embodiments of the invention can also be practiced with other types of devices such as those employing dedicated digital circuitry.

FIG. 2 is a functional, block diagram of the lead monitoring system in which the methods included in the embodiments of the invention can be implemented. The system 30 includes an IMD 10 that utilizes leads (see FIG. 1) for sensing, monitoring, and/or stimulation. The system includes a programmer or other instrument 20 which can communicate with the IMD 10 telemetrically 36 via a wand or programming head, for example. Additional data storage 38 can be provided. The instrument 20 includes a display screen and input keys (not shown) through which a user, such as a physician or clinician, can communicate with the IMD 10 and extract data from the IMD 10. The instrument 20 can also be operatively coupled to a remote computer (not shown) to allow a user at a different location to view the data extracted from the IMD 10. In other embodiments, the IMD 10 can communicate with an additional unit, such as a device located in the patient's home. The device communicates with and can be interrogated by the instrument. Thus, as an example, a patient can download information collected by the IMD every night to a device located on a nightstand, for example. The information stored in the device can be retrieved from the device by the instrument on a regular basis.

As can be seen from FIG. 2, device 10 comprises a primary stimulation control circuit 200 for controlling the device's pacing, monitoring, and sensing functions. The circuitry associated with stimulation control circuit 200 can be of conventional deign, in accordance, for example, with what is disclosed in U.S. Pat. No. 5,052,388, the contents of which are incorporated herein by reference. Stimulation control circuit 200 can include sense amplifier circuitry 240, stimulating pulse output circuitry 260, a crystal clock 280, a random-access memory and read-only memory (RAM/ROM) unit 300, and a central processing unit (CPU) 320, all of which are well known it the art. Device 10 can also include an internal communication circuit 340 so that it is capable of communicating with external instrument unit 20.

With continued reference to FIG. 2, device 10 is coupled to one or more leads 14 which, when implanted, extend transvenously between the implant site of device 10 and the patient's heart 16. Physically the connection between leads 14 and the various internal components of device 10 are facilitated by way of conventional connector block assembly 11, shown in FIG. 1. Electrically, the coupling of the conductors of leads and internal electrical components of device 10 can be facilitated by way of a lead interface circuit 190 which functions, in a multiplexer-like manner, to selectively and dynamically establish necessary connections between various conductors in leads 14, including, for example, atrial tip and ring electrode conductors and ventricular tip and ring electrode conductors and individual electrical components of device 10. For sake of clarity, the specific connections between leads 14 and the various components of device 10 are not shown in FIG. 2, although it will be clear to those of ordinary skill in the art that, for example, leads 14 will necessarily be coupled, either directly or indirectly, to sense amplifier circuitry 240 and stimulating pulse output circuit 260, in accordance with common practice, such that cardiac electrical signals can be conveyed to sensing circuitry 240, and such that stimulating pulses can be delivered to cardiac tissue, via leads 14. Also, not shown in FIG. 2, is the protection circuitry commonly included implanted devices to protect, for example, the sensing circuitry of the device from high voltage stimulating pulses.

As previously noted, stimulation control circuit 200 includes central processing unit 320, which can be an off-the-shelf programmable microprocessor or microcontroller or a custom integrated circuit. Although specific connections between CPU 320 and other components of stimulation control circuit 200 are not shown in FIG. 2, CPU 320 can function to control the timed operation of stimulating pulse output circuit 260 and sense amplifier circuit 240 under control of programming stored in RAM/ROM unit 300.

With continued reference to FIG. 2, crystal oscillator circuit 280 provides main timing clock signals to stimulation control circuit 200. Again, the lines over which such clocking signals are provided to the various timed components of device 10 (e.g., microprocessor 320) are omitted from FIG. 2 for the sake of clarity. Further, it is to be understood that the various components of device 10 depicted in FIG. 2 are powered by means of a battery (not shown) that is contained within the hermetic enclosure of device 10.

Stimulating pulse output circuit 260, which functions to generate cardiac stimuli under control of signals issued by CPU 320, can be any suitable type. Those of ordinary skill in the art could select from among many types of prior art pacing output circuits that would be suitable for the purposes of practicing the embodiments of the invention.

Sense amplifier circuit 240, which can be of conventional design, functions to receive electrical cardiac signals from leads 14 and to process such signals to derive event signals reflecting the occurrence of specific cardiac electrical events, including atrial contractions (P-waves) and ventricular contractions (R-waves). Sensed amplifier 240 provides these event-indicating signals to CPU 320 for use in controlling the synchronous stimulating operations of device 10. In addition, these event-indicating signals can be communicated, via uplink transmission, to external programming unit 20 for visual display to a physician or clinician. Those of ordinary skill in the art will appreciate that device 10 can include numerous other components and subsystems, for example, activity sensors and associated circuitry.

As is well known in the art, the instrument 20 and IMD 10 each have a processor and memory (not shown) for running applications to support the specific IMD and perform the required data collection and analysis for the system as will be discussed in detail hereinafter. In particular, in use, the instrument can download a software routine into an executable RAM space of the IMD for the execution by the IMD's resident firmware. Alternatively, the IMD 10 can have the software already loaded therein as an available feature of the device.

The embodiments of the invention provide the ability to search for and discover data patterns that can indicate a lead-related event using programmable surveillance parameters, the ability to adjust the sampling rates at which the surveillance parameters are measured, the ability to measure other parameters based upon discovered data patterns, as well as the ability to store data patterns for automatic or subsequent diagnosis.

The embodiments of the invention provide the ability to search for and discover data patterns that can indicate a lead-related event(s) using programmable surveillance parameters. Currently devices sample lead(s) impedance infrequently and detect if any of the sampled measurements is outside a lower and upper threshold or reference value and either store the data for later retrieval, and/or change the pacing or cardioversion/defibrillation path, and/or adjust the delivered pacing energy, and/or alert the patient. Comparison of a lead impedance measurement taken at a particular point in time to a fixed range of acceptable values or a fixed reference value can be useful in detecting a lead-related condition that has already manifested itself as an extremely high or low impedance. This, however, generally does not allow gradually occurring lead-related conditions to be detected early on. Moreover, defining a fixed range more narrowly can result in undesired false positives detections thereby causing a clinician to spend time investigating a problem that does not truly exist. Currently devices will look for a data trend in threshold crossings that is linear or exponential before increasing their sampling rate. It has been found through the canine studies that lead-related conditions cannot exhibit a data trend that continuously increases or decreases linearly or exponentially. Rather the lead-related data can exhibit an oscillating pattern that would not be detected by sampling data at lower rates even if threshold crossings are monitored at that lower sampling rate.

Figure 3:
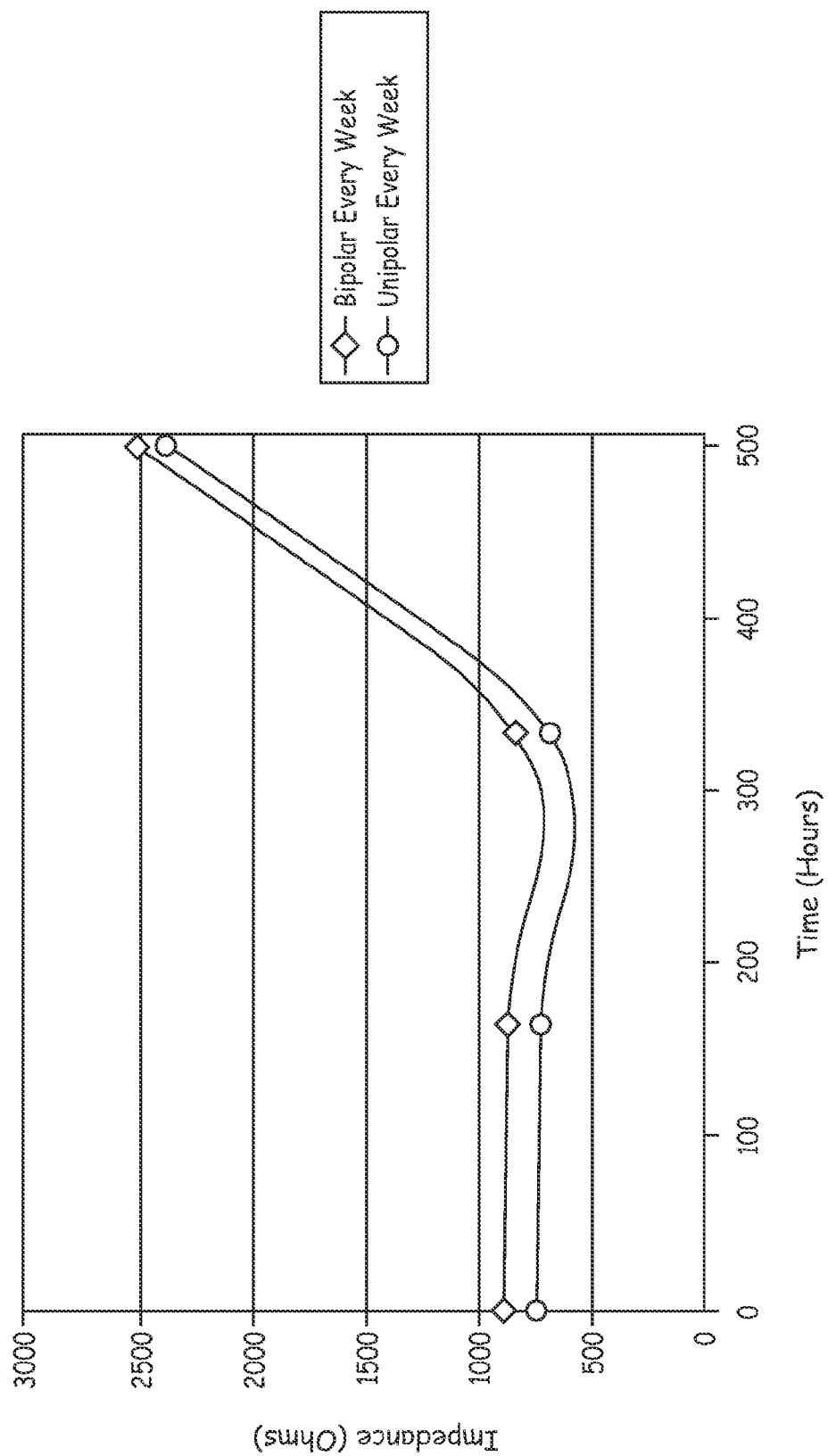
FIGS. 3-6 are graphs of data collected from a canine study at different sampling rates.
Figure 4:
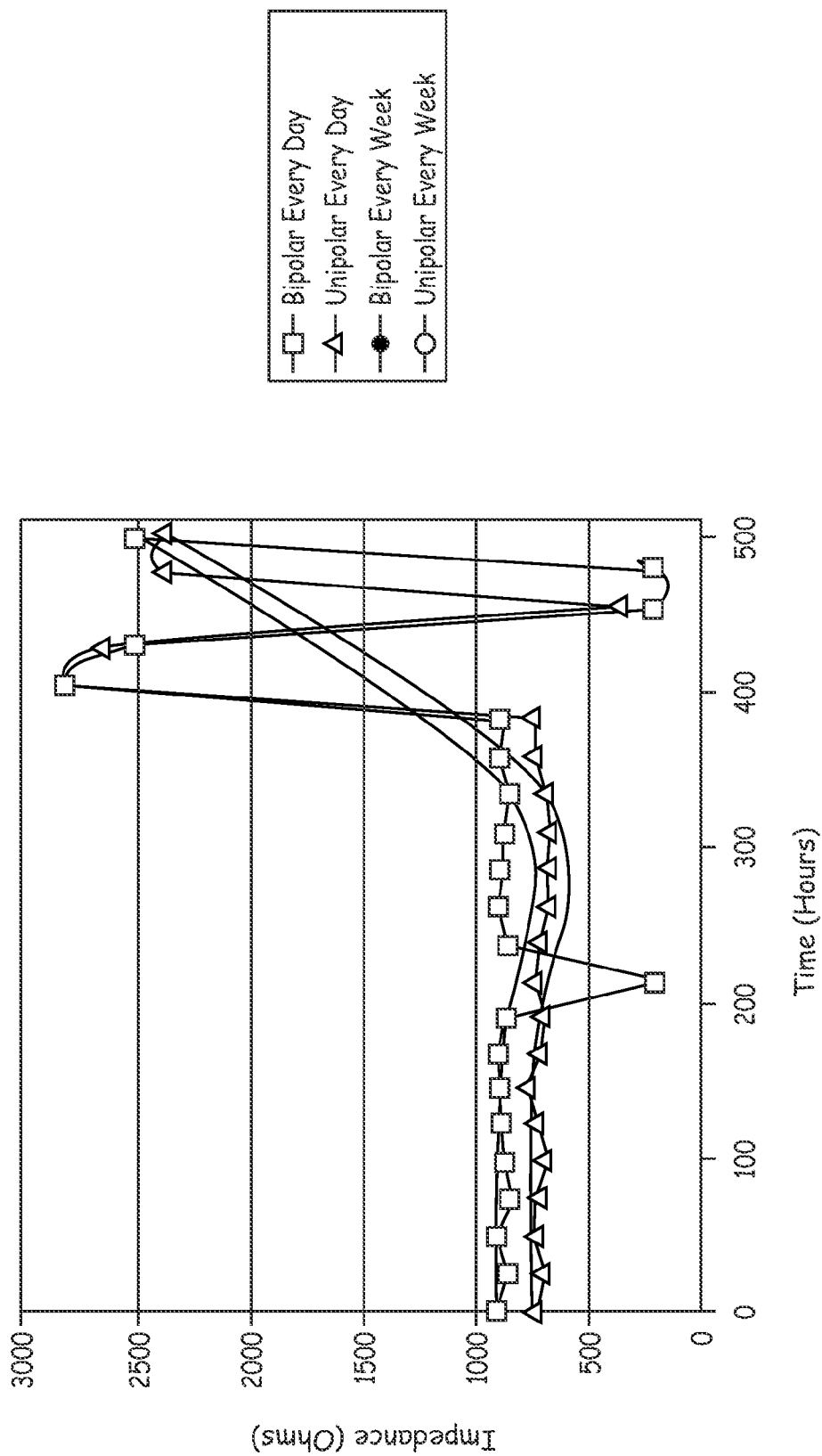
Figure 5:
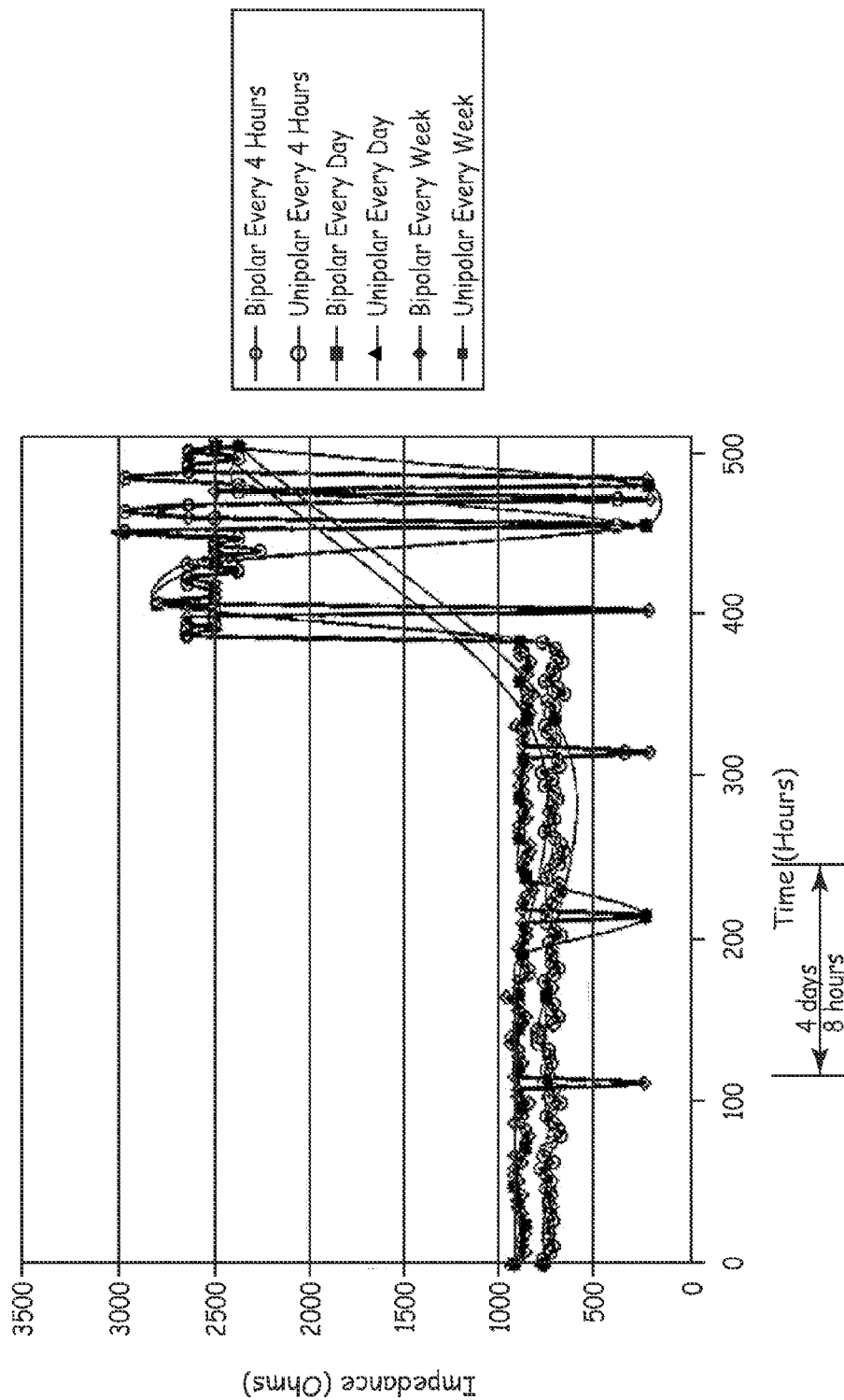
Figure 6:
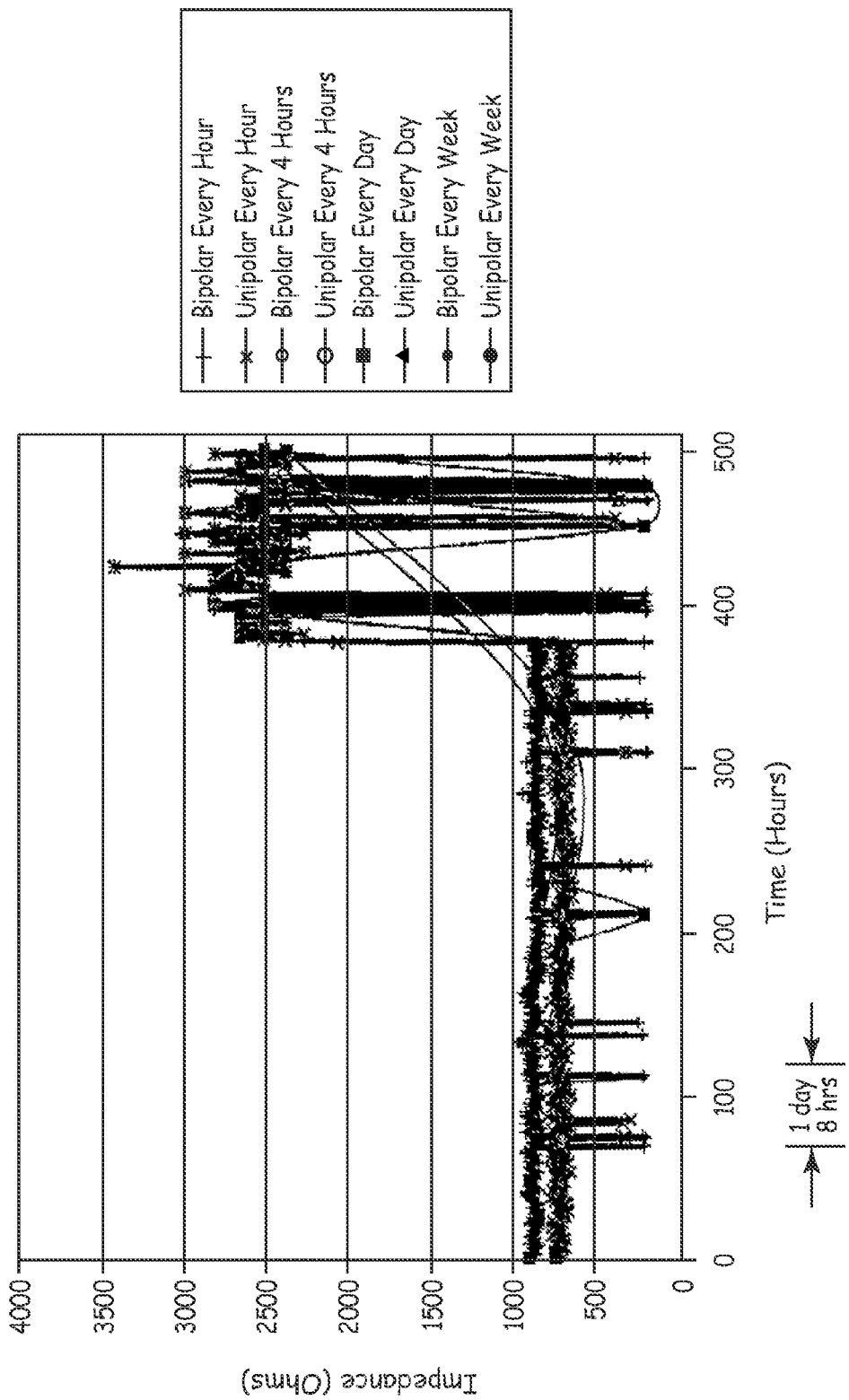

In particular, it has been found through experiments conducted on live canines that collecting lead-related data as well as other data at sampling rates that are higher than rates currently being used, detects oscillating behaviors in that data that can have otherwise gone unnoticed. FIGS. 3-6 illustrate graphs of data collected in experimental studies on live canines for the same measurement interval. Each graph shows the same data collected at a particular sampling rate. FIG. 3 shows data collected at a sampling rate of once a week. FIG. 4 shows data collected at a sampling rate of once a day. FIG. 5 shows data collected at a sampling rate of once every four hours. FIG. 6 shows data collected at a sampling rate of once every hour. In the graphs shown in FIGS. 3-6 unipolar and bipolar impedance measurement data was collected, however, other data can be collected. In FIG. 3, which shows impedance measurements collected once a week, a lead-related condition, i.e., a dramatic increase in impedance, is not indicated until the $16^{th}$ day of monitoring. In FIG. 4, which shows impedance measurements collected once a day, lead-related conditions are indicated as early as the eighth day of monitoring. FIG. 5 which shows impedance measurements collected once every four hours, lead-related conditions are indicated occurring as early as the fourth day of monitoring and FIG. 6 which shows impedance measurements collected once every hour, events are indicated as occurring just after one day of monitoring. Thus, it can be seen from these graphs that increased sampling rates discloses lead events much sooner so that a lead related condition can be detected and monitored before significant degradation or failure in the lead. In fact, comparing the data shown in FIG. 3 and that shown in FIG. 6, one would not have known of the lead-related conditions that were occurring after just one day using the slower sampling rate of the data collected for the graph shown in FIG. 3.

An initial increased sampling rate established prior to detection of a rising trend, for example, will increase the probability of detecting oscillating behaviors that can not be detected at a lower sampling frequency at all prior to a performance issue in a lead. The initial increased sampling frequency will, therefore, not only increase the probability of earlier detection, but increase the probability of any detection prior to a final event such as a complete failure. The FIGS. 3 through 6 show this kind of oscillating behavior and also illustrate very well the delay in detection if only a threshold is monitored. FIGS. 3 through 6 also illustrate an oscillating behavior that will be captured with increased sampling frequency that can be associated with a particular kind of lead condition which might then be able to be used to inform the clinician of the remaining lead life. The ability to detect oscillating behaviors and other lead-related behaviors, which are captured, assist the clinician to predict conditions that can indicate a lead end of life condition or a sustained condition of the lead, which should be monitored over time.

As shown in the comparison of FIGS. 3-6, leads can exhibit particular patterns that are only detectable using higher sampling rates before there is a noticeable reason to increase the sampling rate. Normal surveillance sampling rates can not capture the information necessary to trigger higher sampling rates, which are needed to detect and predict impending lead conditions. The information necessary to trigger higher sampling rats can initially be evident or detectable in time periods between measurement samples during normal surveillance sampling rates. Embodiments of the invention search for crucial information necessary to trigger increased surveillance sampling rates.

To capture surveillance parameters and make them useful as a monitoring, detecting and diagnosing tool, templates of lead-related data are created. These templates include data from specified parameters for specified measurement intervals. Initially, a baseline template is created. The parameters specified for a template can include impedance, wave morphology, slew, sense/pace counters such as reversion, short-circuit pace, open circuit pace, non-physiologic sense, premature ventricular contraction (PVC), loss of capture, capture intervals, and durations, acceleration, activity sensor data, heart rates, pressure, stress, strain, oxygen saturation, enzyme activity, for example. Input from other IMD algorithms such as mode switch, polarity switch, rate response, sensing integrity, and sensing assurance, for example, can also be collected.

In an embodiment of the invention, a template is defined to be a digitalized representation of data patterns or sequences of lead-related data that can be stored in a memory either internal to or external of the IMD 10. The template lead relevant information will be pattern(s) and/or sequences(s) composed of digitized data representing quantified levels of measurable values. The template lead relevant information can be composed of any lead related characteristics including, but not limited to, amplitude thresholds, impedance, open circuits, short circuits, pressure, stress, and other electrical, fluid, and/or mechanical characteristics. As lead technology advances are made, the lead relevant information, which can be collected, will expand and the embodiments of the invention are not limited to the information identified here. As previously described, the data is collected at a particular sampling rate.

The template can be established as part of a power-up sequence by the user or clinician, through data parameter collection during a specified period of time, and/or through adjustment of an existing template. The template can be used to provide a baseline from which to evaluate patterns or sequences of sampled data at subsequent points in time or periods of time as will be described hereinafter. The embodiments of the invention can use one or more templates to provide the desired capability to enable correlations with and comparisons to incoming data patterns and sequences.

The composition of the template can change and preferably does change over the life of the IMD 10. The initial content of a template can change periodically as lead related information changes or new information is captured. Initially, the template can be a representation of normal patterns for a particular patient or a particular lead model or can be a default set of data parameters established at the time of initial execution by the device/instrument or by the user/clinician. Additional templates can be representations of pattern sets based on degraded, defective, normal and/or abnormal lead behaviors, or other physiologic states. These can be obtained by experimentation, by capturing behaviors while monitoring, or can be based on simulated behaviors, or on analysis of existing lead related data. Multiple templates can be used to monitor deviations from normal and to monitor for particular behaviors associated with multiple sets of varied data parameters through correlation. A correlation can encompass a comparison between deviations between a data template and an incoming data pattern for one or more parameters as well as combinations of comparisons. Consequences of correlations and analysis can lead to template composition adjustments.

The template can be initially constructed through self-generation based on an initial set of data patterns and sequences stored as constant values or default values already contained in the IMD 10. Optionally, the template can be initialized by the clinician/user prior to execution based on patient profile information or research data.

A template can be initially updated prior to initial use in comparison and analysis through a collection of sampled lead relevant information from the lead or leads. As previously, discussed, various measurement and monitor data parameters can be collected to build a template or multiple templates. For example, an impedance template can be created as well as a threshold template. For example, the lead(s) can be implanted in a body and information is collected from the implanted lead(s) to initialize the template. Templates generated from incoming data patterns from the leads can represent normal data patterns or data patterns collected to capture abnormal behaviors. In each case the template can be used to track deviations from the normal and/or from the abnormal.

The template plots the monitored or measured data parameter(s) against time. The template will contain data patterns associated with time, which will enable incoming data patterns to be compared not only in terms of quantifiable amplitude or level, but in terms of intervals measured in increments of time. Correlations and comparisons can include, but are not limited to, statistical analysis of deviations over time, pattern recognition techniques, threshold comparisons, amount of change (delta) and/or rate of change behaviors.

The sampling rate is the frequency that data parameters or sets of data parameters are measured. The sampling rate can be initialized in much the same manner as the template, i.e. with a default value on a power up or initial execution or by the user/clinician through a user interface. The sampling rate at which the parameter information is collected can then be updated through an interface to the user or be done automatically. The sampling rate can be adjusted manually or automatically depending on events detected as will be described hereinafter. The sampling rate can be adjusted automatically as a result of automatic analysis and interpretation of correlations and comparisons between data templates and incoming data patterns. The sampling rate can remain the same in some cases and a notification can be sent to an external destination.

A template, yet to be initialized with captured lead related information for the leads, can be used to establish normality for that particular patient or lead model. Once normality for a particular lead is established at a particular point in time, that template can be used as a baseline template to monitor deviations from that normality. The term baseline template refers to an initialized template or any template or templates subsequently created that is used to evaluate data obtained after the creation of the baseline template to which it is being evaluated. Deviations can indicate a new normality or can indicate a new lead related condition or physiological condition. The template content will be used to determine deviations from recently captured lead related information. The deviations with recently captured lead related information will be used to identify lead conditions, lead failures, or to trigger other algorithmic actions, such as increasing sample rates for a particular kind of information. A template initialized with a representation of a particular degraded, defective or abnormal lead behavioral set of characteristics, can be used as a trigger mechanism if the clinician is monitoring for a behavior indicating an impending condition of failure.

The trigger mechanism can trigger an algorithm to increase/decrease sampling for a particular measurement of lead related information, such as pressure, threshold, or impedance. The trigger mechanism can trigger the algorithm to notify the clinician of a condition. The trigger is defined to be a decision or mechanism based on a set of criteria composed of automatic or clinical analytical results of template data patterns vs. incoming measured data patterns for one or more templates. A statistical analysis of template data patterns vs. incoming data patterns can comprise the trigger criteria for a sampling rate adjustment. The trigger can also be a decision to adjust the template itself with the latest incoming data patterns.

The embodiments of the invention also provide the ability to adjust the rates at which the surveillance parameters are measured as well as determine if other parameters should be measured and the rates at which those parameters should be sampled.

The system collects data representing a plurality of surveillance parameters that can include impedance and threshold from an active lead implanted in a body at a first sampling rate. The collected data is compared to a baseline template, which initially would represent normal operation of the lead. If the comparison of the plurality of surveillance parameters measured with the baseline template is outside an acceptable range of deviation, then, the plurality of surveillance parameters measured are compared to template adjustment criteria. The adjustment criteria include additional surveillance parameter data that represent factors that can cause the measured parameters being outside an acceptable range of deviation yet need not be interpreted as a lead-related condition. For example, a person can be extremely active during the measurement interval which could be determined by the output of an accelerometer or the oxygen levels detected. This would dictate that comparing the measured surveillance data at that time against the baseline template would not result an accurate detection of a lead related condition. Thus, if the template adjustment criteria are met, the baseline template is replaced with an adjusted template and the adjusted template is used for further comparisons with the measured surveillance parameters. Updating the template used should help to reduce the possibility of false positives that indicate that there can be an issue with the lead when in actuality there is none. Updating the template in such a manner using additional information helps further refine the monitoring process.

If, on the other hand, the adjustment criteria are not met, then, the plurality of surveillance parameters measured are compared with lead surveillance criteria. The surveillance criteria can include templates indicating lead degradation and failure patterns. In addition, lead surveillance criteria indicates when something out of the ordinary is happening with a lead. Known failure mechanisms can be used to identify these criteria and implement them in an algorithm. The lead surveillance criteria can be updated manually or automatically. These patterns can be determined statistically or empirically. The comparison of the plurality of surveillance parameters measured with the lead surveillance criteria will determine what course of action takes place. For example, options include one or more of the following: everything is fine with the lead and nothing needs to be done, adjust the baseline template or replace it with an adjusted template to reflect new lead behavior, inform the user of potential lead issues and increase the sampling rate at which the plurality of surveillance parameters are measured, increase the amount or type of data collected by adjusting the programmable surveillance parameters either manually or automatically.

Figure 7:
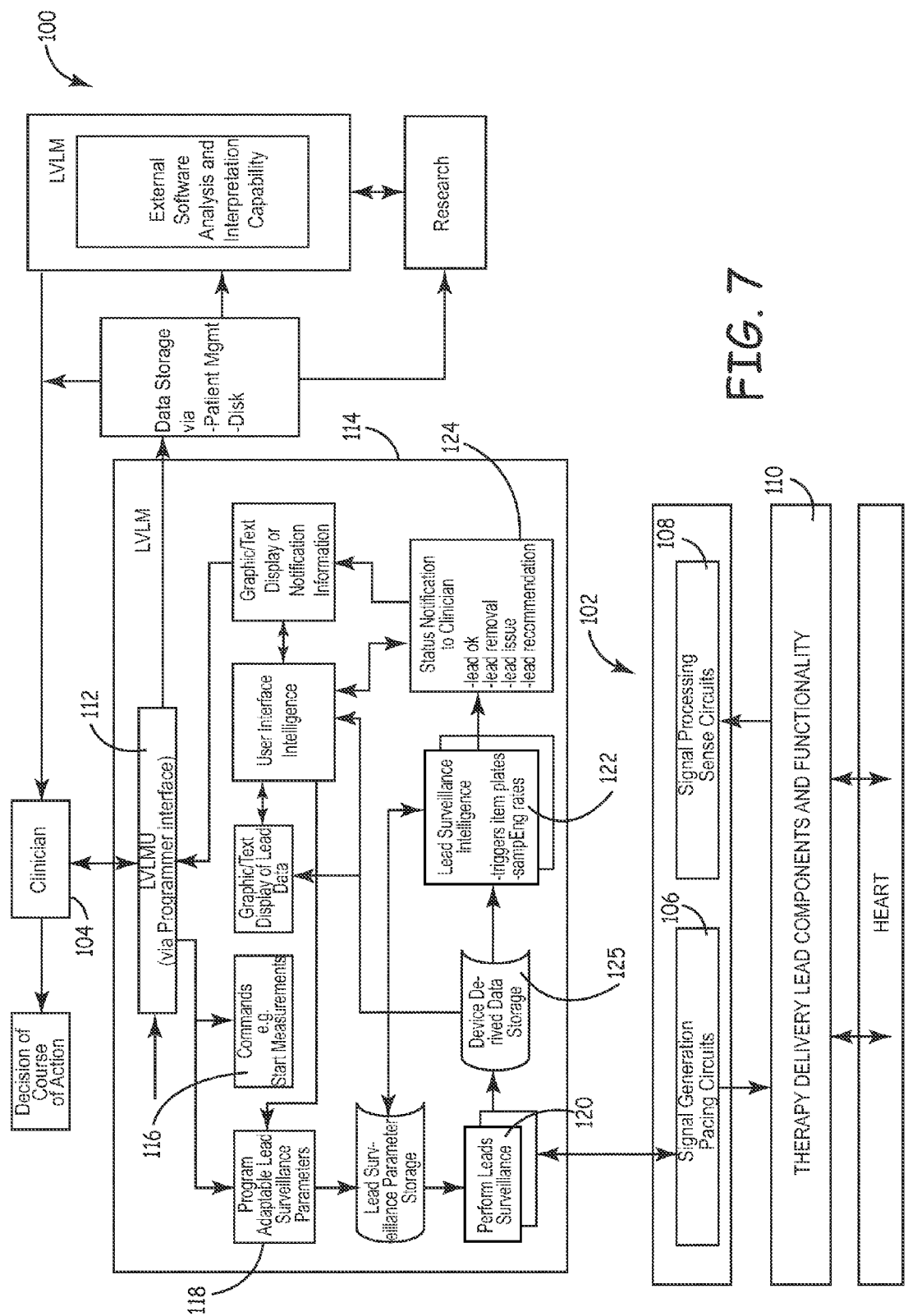
FIG. 7 is a functional block diagram of the overall monitoring system.

FIG. 7 is a functional block diagram of the overall monitoring, detecting and diagnosing system 100. The monitoring/detecting/diagnosing system includes an IMD 102 implanted in a patient and a location 104 remote from the IMD, such as the office of a clinician or physician, for example. The system 100 is shown separately from the IMD but, as previously described, it can be incorporated in the IMD itself. The system interacts with the signal generation pacing circuits 106 and signal processing sense circuits 108 of the IMD which interact with the implanted leads 110. In the particular embodiment illustrated, the system 100 includes an instrument 114 that has a user interface 112 through which a user 104 can interact with the IMD. The instrument 114 allows a user 104 to enter information. That information can include commands 116, such as start and stop measurements, as well as data and control parameters 118. The data parameters can be used to initialize or update one or more templates. The control parameters will characterize the kind of data parameters to be measured and define the environment under which they are collected. Control parameters can include, but not be limited to, pulse width for output pulses, bipolar or unipolar sensing for waveform detection, bipolar or unipolar output pulse generation for impedance data and threshold measurement parameters as examples. Other control parameters can include enable/disable, surveillance sample type such as impedance or threshold, surveillance type distinction such as unipolar or pulse width, selected sample interval, number of samples per measurement set, measurement set period, sensing configuration type, blanking interval, etc Control parameters will also establish initial and updated sampling rates as well as preferred output options.

Other information besides data and control parameters can be incorporated. This information can include such things as lead model, lead configuration, lead location, time and date of lead implant. It can also include IMD model, IMD date of implant, drugs and drug dosages, lead design parameters and change-out information.

At block 118 the lead surveillance parameters have been selected and are stored at block 119 until needed to perform a lead surveillance. When the device is ready to collect lead data, it performs a lead surveillance at block 120 and retrieves data at a sampling rate dictated by the surveillance parameters. Block 120 will implement control parameters which define the conditions under which data parameters are measured, retrieve the measurements, and store the collected data in memory. That collected data information is stored at 215 and can be communicated to block 122, which performs intelligence on the lead surveillance data.

The lead surveillance intelligence (LSI) provides the intelligence to automatically perform lead data pattern analysis and decision making to evaluate lead data templates and trigger points for sampling rate changes, template adjustments, and/or notifications. The LSI will determine automatic template updates and comparisons, trigger updates and comparisons and lead related notifications to the remote location 104. The LSI provides the intelligence to perform decision making automatically, which will lead to immediate adjustments in the templates, sampling rates, and trigger mechanisms without clinician involvement. Adjustments and decisions will be available to the clinician on interrogation or because of instant or periodic communications when required.

The LSI can perform mathematical manipulations and calculations based on the measurement and input parameters measured such as determining minimums, maximums, averages, deviations, deltas, trending, percentage matches, ratios, derivatives, integrals, pattern recognition and correlations, for example. For example, the following calculations can be made as described in the below table.

| Controlled Parameters | Description |
| --- | --- |
| Calculate max, min, average of threshold from the raw data | User capability to request the max, min and average thresholds be computed from the threshold data set retrieved. The max, min and average thresholds will be computed for each measured pulse width used during threshold measurements. Values will be displayed to the user. The max, min and average thresholds will be stored temporarily in the user interface and displayed on the screen. They will be downloaded to the diskette when requested. |

| Controlled Parameters | Description |
|---|---|
| Calculate greatest delta between threshold measurements | User capability to request the greatest delta between thresholds be computed from the threshold data set at all requested pulse widths. Values will be displayed to the user. They will be stored temporarily in the user interface and displayed on the screen. They will be downloaded to the diskette when requested. |
| Calculate max, min, average Chronaxie | User capability to request the max, min and average Chronaxie values be computed from the threshold data set. Values will be displayed to the user. The max, min and average will be stored temporarily in the user interface and displayed on the screen. They will be downloaded to the diskette when requested. |
| Calculate Total count per error code | User capability to display total counts for any aborts. Values will be displayed to the user. They will be stored temporarily in the user interface and displayed on the screen. They will be downloaded to the diskette when requested. |
| Calculate max, min, average impedance | User capability to request max, min and average impedance be computed for each lead in both the bipolar and unipolar configurations from the impedance data set retrieved by the user interface. Values will be displayed to the user. The max, min and average will be stored temporarily in the user interface and displayed on the screen. They will be downloaded to the diskette when requested. |
| Calculate greatest delta between impedance measurements | User capability to request the greatest delta be computed between raw data impedance measurements in both the bipolar and unipolar configurations. Values will be displayed to the user. They will be stored temporarily in the user interface and displayed on the screen. They will be downloaded to the diskette when requested. |
| Calculate max, min, average R wave | User capability to request max, min and average values for R wave amplitudes from the signal data set. Values will be displayed to the user. The max, min and average will be stored temporarily in the user interface and displayed on the screen. They will be downloaded to the diskette when requested. |
| Calculate max, min, average P wave | User capability to request max, min and average values for P wave amplitudes from the signal data set be computed Values will be displayed to the user. The max, min and average will be stored temporarily in the user interface and displayed on the screen. They will be downloaded to the diskette when requested. |
| Calculate max, min, average FFR wave | User capability to request max, min and average values for FFR wave amplitudes from the signal data set be computed Values will be displayed to the user. The max, min and average will be stored temporarily in the user interface and displayed on the screen. They will be downloaded to the diskette when requested. |
| Calculate max, min, average PR Interval | User capability to request max, min and average values for PR intervals from the signal data set be computed. Values will be displayed to the user. The max, min and average will be stored temporarily in the user interface and displayed on the screen. They will be downloaded to the diskette when requested. |
| Calculate max, min, average QRS Interval | User capability to request max, min and average values for QRS intervals from the signal data set be computed. Values will be displayed to the user. The max, min and average will be stored temporarily in the user interface and displayed on the screen. They will be downloaded to the diskette when requested. |
| Calculate max, min, average Slew | User capability to request max, min and average values for slew rates from the signal data set be computed. Values will be displayed to the user. The max, min and average will be stored temporarily in the user interface and displayed on the screen. They will be downloaded to the diskette when requested. |

At block 124 that information as well as status notification is sent to the remote location 104. Various types of notifications can be made such as lead is ok, lead needs to be removed, there is an issue with the lead or a recommendation concerning the lead and this information can be conveyed graphically to the user at the user interface of the instrument.

More particularly, the embodiments of the invention provide the ability to search, discover, and capture patterns of behavior that will trigger higher surveillance sampling rates needed to characterize relevant patterns of behavior and to trigger surveillance of lead related parameters that can not have been under surveillance initially.

The preceding specific embodiments are illustrative of the practice of the invention. Various modifications can be made without departing from the scope of the claims. For example, the invention can be practiced by a variety of implantable medical devices.

The invention can be embodied as a computer-readable medium that includes instructions for causing a programmable processor to carry out the methods described above. A "computer-readable medium" includes but is not limited to read-only memory, Flash memory and a magnetic or optical storage medium. The instructions can be implemented as one or more software modules, which can be executed by themselves or in combination with other software.

These and other embodiments are within the scope of the following claims.

What is claimed is:

1. A method for detecting a lead-related condition, comprising:
    collecting a first set of data of a plurality of medical electrical lead surveillance parameters at a first data sampling rate from an active implantable medical device (IMD) implanted in a subject;
    concurrently comparing the collected plurality of surveillance parameters to a baseline template and evaluating any deviation, wherein the baseline template is a digitized representation of data patterns or sequences of lead-related data, wherein said baseline template includes a similar plurality of medical electrical lead surveillance parameters from the active IMD implanted in the subject; and deriving an indication of lead failure from the deviation.

2. A method according to claim 1, wherein if the deviation is greater than a first threshold then:

evaluating template adjustment criteria, wherein the template adjustment criteria include additional surveillance parameter data;

replacing the baseline template with an adjusted baseline template if the template adjustment criteria are met.

3. A method according to claim 2, further comprising comparing the plurality of surveillance parameters collected with lead surveillance criteria if the adjustment criteria are not met, wherein the lead surveillance criteria include templates of at least one of: representations of degraded lead characteristics, defective lead characteristics.

4. A method according to claim 2, wherein the adjustment criteria include analyzing additional surveillance parameter data.

5. A method according to claim 4, wherein the additional surveillance parameter data include at least one of: a wave morphology metric, a slew metric, a sense/pace counter metric, a short-circuit pace event metric, an open circuit pace metric, a non-physiologic sense metric, a premature ventricular contraction (PVC) metric, a loss of capture metric, a capture interval metric, a capture duration metric, a heart wall acceleration metric, an activity sensor data metric, a heart rate metric, a blood pressure metric, a stress metric, a strain metric, an oxygen saturation metric, an enzyme activity metric.

6. A method according to claim 1, wherein the IMD comprises:

a pacemaker, an implantable cardioverter-defibrillator, a neurological stimulation device, a deep brain stimulation device, a muscle stimulation device, an implantable pulse generator, an active medical device coupled to at least one elongated medical electrical lead.

7. A method according to claim 1, further comprising:

storing one of the collected parameters and the results of the compared parameters in a memory structure.

8. A method according to claim 1, further comprising telemetering a status notification of the deviation.

9. A method according to claim 1, wherein the baseline template is created by:

selecting default programmable surveillance parameters;

inputting values for the default programmable surveillance parameters; and creating the baseline template from the values for the default programmable surveillance parameters for a particular data collection interval.

10. An apparatus for detecting a lead-related condition, comprising:

means for collecting a first set of data of a plurality of medical electrical lead surveillance parameters from an active implantable medical device (IMD) implanted in a subject;

means for concurrently comparing the collected plurality of lead surveillance parameters to a baseline template to evaluate any deviation, wherein the baseline template is a digitized representation of data patterns or sequences of lead-related data, wherein said baseline template includes a similar plurality of medical electrical lead surveillance parameters from the active IMD implanted in the subject; and means for determining whether the deviation is indicative of lead failure.

11. An apparatus according to claim 10, wherein if the deviation is greater than a first threshold value further comprising:

means for comparing template adjustment criteria to the plurality of surveillance parameters collected; and means for replacing the baseline template with an adjusted baseline template.

12. An apparatus according to claim 11, further comprising means for comparing the collected plurality of surveillance parameters with lead surveillance criteria if the adjustment criteria are not met, wherein the lead surveillance criteria include templates of at least one of:

representations of degraded lead characteristics, defective lead characteristics.

13. An apparatus according to claim 11, wherein the adjustment criteria include analyzing additional surveillance parameter data.

14. An apparatus according to claim 13, wherein the additional surveillance parameter data include at least one of: a wave morphology metric, a slew metric, a sense/pace counter metric, a short-circuit pace event metric, an open circuit pace metric, a non-physiologic sense metric, a premature ventricular contraction (PVC) metric, a loss of capture metric, a capture interval metric, a capture duration metric, a heart wall acceleration metric, an activity sensor data metric, a heart rate metric, a blood pressure metric, a stress metric, a strain metric, an oxygen saturation metric, an enzyme activity metric.

15. A method for detecting a lead related condition comprising:

defining a plurality of medical electrical lead surveillance parameters;

defining a first sampling rate for each of the plurality of surveillance parameters, wherein each of the sampling rates is independent of the other sampling rates;

creating a patient specific baseline template, wherein the baseline template is a digitized representation of data patterns or sequences of lead-related data, wherein the method of creating the template comprises:

collecting a first set of data of the plurality of surveillance parameters at the defined sampling rates; and generating a patient specific template based on the first set of data;

diagnosing the lead related condition, wherein the method of diagnosing comprises:

collecting a second set of data of the plurality of surveillance parameters at the defined sampling rates; and concurrently comparing the second set of data to the baseline template to evaluate any deviation; and determining whether the deviation is indicative of lead failure.

16. A method according to claim 15, further comprising telemetrically communicating a status notification based on the deviation.

17. A method according to claim 15, further comprising evaluating template adjustment criteria if the deviation is greater than a first threshold value, wherein the template adjustment criteria includes data from at least one of: an accelerometer, an oxygen sensor.

18. A method according to claim 17, further comprising adjusting the patient specific baseline template with the collected surveillance parameters if the template adjustment criteria are met.

19. A method according to claim 15, wherein the step of determining whether the deviation is indicative of lead failure includes:

selecting one or more of the plurality of surveillance parameters;

defining a second sampling rate for each of the plurality of surveillance parameters, wherein the second sampling rate is greater than the first sampling rate;

collecting a third set of data of one or more of the selected plurality of surveillance parameters at the second sampling rate; and comparing the third set of data to lead surveillance criteria, wherein the lead surveillance criteria include templates of at least one of: representations of degraded lead characteristics, defective lead characteristics.

20. A method according to claim 15, wherein the surveillance parameter data include at least one of: impedance, threshold, pressure.

* * * * *